United States Patent
Green et al.

(10) Patent No.: US 9,410,100 B2
(45) Date of Patent: Aug. 9, 2016

(54) TRITYLATED ETHERS

(71) Applicant: ANGUS Chemical Company, Buffalo Grove, IL (US)

(72) Inventors: George David Green, Cary, IL (US); Raymond Swedo, Mount Prospect, IL (US)

(73) Assignee: Dow Global Technologies LLC, Midland, MI (US)

( * ) Notice: Subject to any disclaimer, the term of this patent is extended or adjusted under 35 U.S.C. 154(b) by 88 days.

(21) Appl. No.: 14/398,751

(22) PCT Filed: Apr. 26, 2013

(86) PCT No.: PCT/US2013/038378
§ 371 (c)(1),
(2) Date: Nov. 4, 2014

(87) PCT Pub. No.: WO2013/165839
PCT Pub. Date: Nov. 7, 2013

(65) Prior Publication Data
US 2015/0128485 A1  May 14, 2015

Related U.S. Application Data

(60) Provisional application No. 61/642,560, filed on May 4, 2012.

(51) Int. Cl.
*C10L 1/18* (2006.01)
*C10L 1/185* (2006.01)
*C07C 43/23* (2006.01)
*C10L 1/00* (2006.01)

(52) U.S. Cl.
CPC ............. *C10L 1/1852* (2013.01); *C07C 43/23* (2013.01); *C10L 1/003* (2013.01); *C10L 2200/0453* (2013.01); *C10L 2230/16* (2013.01); *C10L 2290/24* (2013.01)

(58) Field of Classification Search
CPC .................. C10L 1/1852; C10L 1/003; C10L 2200/0453; C10L 2230/16; C10L 2290/24; C07C 43/23
See application file for complete search history.

(56) References Cited

U.S. PATENT DOCUMENTS

| | | | |
|---|---|---|---|
| 5,981,283 | A | 11/1999 | Anderson, II et al. |
| 7,858,373 | B2 | 12/2010 | Banavali et al. |
| 2012/0090225 | A1 | 4/2012 | Green et al. |
| 2014/0123549 | A1 | 5/2014 | Green et al. |

FOREIGN PATENT DOCUMENTS

| | | |
|---|---|---|
| EP | 512404 A1 | 11/1992 |
| WO | WO2012154646 A1 | 11/2012 |
| WO | WO2012154668 A1 | 11/2012 |

OTHER PUBLICATIONS

Eiichi Funakubo et al., Studies on the Utilisation of the Camphor Oil. Il Nippon Kagaku Kaishi, vol. 58 (1937) No. 11 pp. 1241-1243.*
Iddles, et al, "Rearrangement of the Triphenylmethyl Ether of Ortho Cresol: Direct Synthesis of 3-Methyl-4-methoxyphenyltriphenylmethane", J. Am. Chem. Soc., vol. 62, No. 10, pp. 2757-2759 (1940).
Chuchani, et al., "Kinetics and Substituent Effects in Electrophillic", J. Organic Chemistry, vol. 31, No. 5, pp. 1573-1576 (1966).
Clapp, "The Aldehydic Constituents from the Ethanolysis of Spruce and Maple Woods", J. Am. Chem. Soc., vol. 61, No. 2, pp. 523-524 (1939).
Index of subjects, J. Chem. Soc. (Resumed), p. 3012 (1929).
Schoepfle, et al., "The Reaction between Triarylmethyl Halides and Phenyimagnesium Bromide. II", vol. 58, pp. 791-794 (1936).
Llewellyn, et al., "The Condensation of Some Tertiary Aryl Substituted Carbinols with Phenol in the Presence of Aluminum Chloride", vol. 60, pp. 59-62 (1938).
Barroeta, et al., "Kinetics and Substituent Efflects in Electrophillic Aromatic Substitution. II. Tritylation of Catechol and its Monoether", vol. 31, pp. 2330-2333 (1966).
Agarwal, et al., "Studies on polynucleotides. CXLIII. A rapid and convenient method for the synthesis of deoxyribooligonucleotides carrying 5'-phosphate end groups using a new portecting group", J. Amer. Chem. pp. 1065-1072 (1976).
Anelli, et al., "Toward Controllable Molecular Shuttles", Chem. European Journal, vol. 3, No. 7, pp. 1113-1135 (1997).
Ballardini, et al., "Molecular Meccano, 56 Anthracene-Containing [2]Rotaxanes: Synthesis, Spectroscopic, and Electrochemical Properties", J. Chem European, pp. 591-602 (2000).
Galanin, et al., "Synthesis and Properties of [4-(Triphenylmethyl) phenoxy]acetic and 3-[4-(Triphenylmethyl)phenoxy] propionic Acids and Their Condensation wiht Phthalimide Leading to meso-Substituted Tetrabenzoporphyrins", Russian J. Chem., vol. 45, No. 7 pp. 1024-1030 (2009).
Fayez, et al., "Reaction of Phosphonium Ylides with 4-Triphenylmethyl-1, 2-benzoquinone", Tetrahedron, vol. 49, No. 38, pp. 8691-8704 (1993).

* cited by examiner

*Primary Examiner* — Cephia D Toomer
(74) *Attorney, Agent, or Firm* — Kenneth Crimaldi

(57) ABSTRACT

A compound having formula $(Ph_3C)_mAr(GR)_n$, wherein Ph represents a phenyl group, Ar is an aromatic ring system having from six to twenty carbon atoms; G is O, S, SO or $SO_2$; R is: (a) $C_1$-$C_{18}$ alkyl substituted by at least one of OH, SH, $C_1$-$C_{18}$ alkoxy and cyano; or (b) $C_4$-$C_{18}$ heteroalkyl; m is one or two; and n is an integer from one to four.

11 Claims, No Drawings

TRITYLATED ETHERS

This invention relates to new compounds useful in a method for marking liquid hydrocarbons and other fuels and oils.

Marking of petroleum hydrocarbons and other fuels and oils with various kinds of chemical markers is well known in the art. A variety of compounds have been used for this purpose, as well as numerous techniques for detection of the markers, e.g., absorption spectroscopy and mass spectrometry. For example, U.S. Pat. No. 7,858,373 discloses the use of a variety of organic compounds for use in marking liquid hydrocarbons and other fuels and oils. However, there is always a need for additional marker compounds for these products. Combinations of markers can be used as digital marking systems, with the ratios of amounts forming a code for the marked product. Additional compounds useful as fuel and lubricant markers would be desirable to maximize the available codes. The problem addressed by this invention is to find additional markers useful for marking liquid hydrocarbons and other fuels and oils.

STATEMENT OF INVENTION

The present invention provides a compound having formula $(Ph_3C)_mAr(GR)_n$, wherein Ph represents a phenyl group, Ar is an aromatic ring system having from six to twenty carbon atoms; G is O, S, SO or $SO_2$; R is: (a) $C_1$-$C_{18}$ alkyl substituted by at least one of OH, SH, $C_1$-$C_{18}$ alkoxy and cyano; or (b) $C_4$-$C_{18}$ heteroalkyl; m is one or two; and n is an integer from one to four.

The present invention further provides a method for marking a petroleum hydrocarbon or a liquid biologically derived fuel; said method comprising adding to said petroleum hydrocarbon or liquid biologically derived fuel at least one compound having formula $(Ph_3C)_mAr(GR)_n$, wherein Ph represents a phenyl group, Ar is an aromatic ring system having from six to twenty carbon atoms; G is O, S, SO or $SO_2$; R is: (a) $C_1$-$C_{18}$ alkyl substituted by at least one of OH, SH, $C_1$-$C_{18}$ alkoxy and cyano; or (b) $C_4$-$C_{18}$ heteroalkyl; m is one or two; and n is an integer from one to four; wherein each compound having formula $(Ph_3C)_mAr(GR)_n$ is present at a level from 0.01 ppm to 20 ppm.

DETAILED DESCRIPTION

Percentages are weight percentages (wt %) and temperatures are in ° C., unless specified otherwise. Concentrations are expressed either in parts per million ("ppm") calculated on a weight/weight basis, or on a weight/volume basis (mg/L); preferably on a weight/volume basis. The term "petroleum hydrocarbon" refers to products having a predominantly hydrocarbon composition, although they may contain minor amounts of oxygen, nitrogen, sulfur or phosphorus; petroleum hydrocarbons include crude oils as well as products derived from petroleum refining processes; they include, for example, crude oil, lubricating oil, hydraulic fluid, brake fluid, gasoline, diesel fuel, kerosene, jet fuel and heating oil. Marker compounds of this invention can be added to a petroleum hydrocarbon or a liquid biologically derived fuel; examples of the latter are biodiesel fuel, ethanol, butanol, ethyl tert-butyl ether or mixtures thereof. A substance is considered a liquid if it is in the liquid state at 20° C. A biodiesel fuel is a biologically derived fuel containing a mixture of fatty acid alkyl esters, especially methyl esters. Biodiesel fuel typically is produced by transesterification of either virgin or recycled vegetable oils, although animal fats may also be used. An ethanol fuel is any fuel containing ethanol, in pure form, or mixed with petroleum hydrocarbons, e.g., "gasohol." An "alkyl" group is a substituted or unsubstituted hydrocarbyl group having from one to twenty-two carbon atoms in a linear, branched or cyclic arrangement. Substitution on alkyl groups of one or more OH or alkoxy groups is permitted; other groups may be permitted when specified elsewhere herein. Preferably, alkyl groups are saturated. Preferably, alkyl groups are unsubstituted. Preferably, alkyl groups are linear or branched. An "aryl" group is a substituent derived from an aromatic hydrocarbon compound. An aryl group has a total of from six to twenty ring atoms, unless otherwise specified, and has one or more rings which are separate or fused. Substitution on aryl groups of one or more alkyl or alkoxy groups is permitted. A "heteroalkyl" group is an alkyl group in which one or more methylene groups has been replaced by O or S. Preferably, heteroalkyl groups contain from one to six O or S atoms, preferably from one to four, preferably from one to three. The methylene groups replaced by O or S were bonded to two other carbon atoms in the corresponding alkyl group. Preferably, heteroalkyl groups do not contain S atoms. Heteroalkyl groups may be substituted by OH, SH or $C_1$-$C_{18}$ alkoxy groups, preferably OH or $C_1$-$C_6$ alkoxy groups, preferably hydroxy or $C_1$-$C_4$ alkoxy groups. Examples of heteroalkyl groups include oligomers of ethylene oxide, propylene oxide or butylene oxide having two to six units of the alkylene oxide (preferably two to four, preferably two or three) and a terminal hydroxy or $C_1$-$C_6$ alkoxy group (preferably hydroxy or $C_1$-$C_4$ alkoxy, preferably hydroxy or methoxy, preferably hydroxy); an example of an ethylene oxide oligomer is $—\{(CH_2)_2O\}_jR^2$, where j is an integer from two to six and $R^2$ is hydrogen or $C_1$-$C_6$ alkyl. Preferably, j is from two to four, preferably two or three. Preferably, $R^2$ is hydrogen or $C_1$-$C_4$ alkyl, preferably hydrogen or methyl, preferably hydrogen. Preferably, the compounds of this invention contain elements in their naturally occurring isotopic proportions.

Ar is an aromatic ring system having from six to twenty carbon atoms and whose substituents include $Ph_3C$ and OR groups, preferably one in which the only substituents are $Ph_3C$ and OR groups. Preferably, Ar is a $C_6$-$C_{12}$ hydrocarbyl aromatic ring system. Preferably, Ar is benzene, naphthalene, biphenyl, phenyl ether, diphenylmethane or one of the preceding systems substituted with alkyl and/or alkoxy groups; preferably benzene. Preferably, n is from one to three, preferably two or three, preferably two. Preferably, G is O or S, preferably O. Preferably, R is (a) $C_2$-$C_{18}$ alkyl substituted by at least one of OH, SH, $C_1$-$C_{12}$ alkoxy and cyano, or (b) $C_4$-$C_{18}$ heteroalkyl; preferably (a) $C_3$-$C_{12}$ alkyl substituted by at least one of OH, SH and $C_1$-$C_6$ alkoxy, or (b) $C_4$-$C_{12}$ heteroalkyl; preferably (a) $C_3$-$C_{12}$ alkyl substituted by at least one of OH and $C_1$-$C_6$ alkoxy, or (b) $C_4$-$C_{12}$ heteroalkyl; preferably $C_4$-$C_{18}$ heteroalkyl; preferably $C_4$-$C_{12}$ heteroalkyl; preferably $C_4$-$C_8$ heteroalkyl; preferably $C_4$-$C_6$ heteroalkyl. Preferably, R has a single substituent selected from OH, SH, $C_1$-$C_{18}$ alkoxy and cyano; preferably said single substituent is in a terminal position on R, i.e., on the carbon furthest from Ar. Preferably, when G is O, R is: (a) $C_1$-$C_{18}$ alkyl substituted by at least one of SH and cyano; (b) $C_2$-$C_{12}$ alkyl substituted by OH or $C_1$-$C_{18}$ alkoxy; or (c) $C_4$-$C_{18}$ heteroalkyl; preferably when G is O, R is: (a) $C_1$-$C_{18}$ alkyl substituted by at least one of SH and cyano; (b) $C_2$-$C_{18}$ alkyl substituted by OH or $C_1$-$C_{18}$ alkoxy, said OH or $C_1$-$C_{18}$ alkoxy group being in a terminal position; or (c) $C_4$-$C_{18}$ heteroalkyl; preferably when G is O, R is: (a) $C_1$-$C_{18}$ alkyl substituted by at least one of SH and cyano; (b) $C_2$-$C_{12}$ alkyl substituted by OH or $C_1$-$C_{12}$ alkoxy, said OH or $C_1$-$C_{12}$ alkoxy group being in a terminal position; or (c) $C_4$-$C_{18}$ heteroalkyl; preferably when G is O, R is: (a) $C_1$-$C_{18}$ alkyl substituted by at least one of SH and cyano; or (b) $C_4$-$C_{18}$ heteroalkyl.

Preferably, the compound of this invention is represented by formula (I)

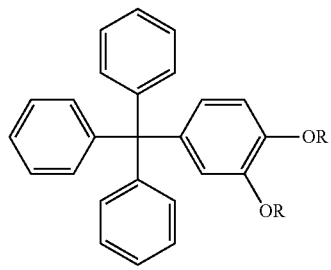

(I)

wherein R is as defined above.

Preferably, the compound of this invention is represented by formula (II)

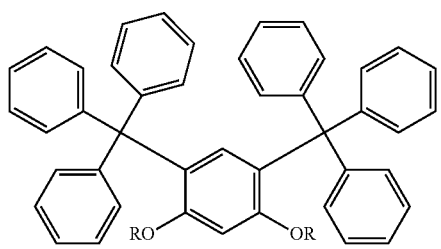

(II)

wherein R is as defined above.

In using the compounds of this invention as markers, preferably the minimum amount of each compound added to a liquid to be marked is at least 0.01 ppm, preferably at least 0.02 ppm, preferably at least 0.05 ppm, preferably at least 0.1 ppm, preferably at least 0.2 ppm. Preferably, the maximum amount of each marker is 50 ppm, preferably 20 ppm, preferably 15 ppm, preferably 10 ppm, preferably 5 ppm, preferably 2 ppm, preferably 1 ppm, preferably 0.5 ppm. Preferably, the maximum total amount of marker compounds is 100 ppm, preferably 70 ppm, preferably 50 ppm, preferably 30 ppm, preferably 20 ppm, preferably 15 ppm, preferably 12 ppm, preferably 10 ppm, preferably 8 ppm, preferably 6 ppm, preferably 4 ppm, preferably 3 ppm, preferably 2 ppm, preferably 1 ppm. Preferably, a marker compound is not detectible by visual means in the marked petroleum hydrocarbon or liquid biologically derived fuel, i.e., it is not possible to determine by unaided visual observation of color or other characteristics that it contains a marker compound. Preferably, a marker compound is one that does not occur normally in the petroleum hydrocarbon or liquid biologically derived fuel to which it is added, either as a constituent of the petroleum hydrocarbon or liquid biologically derived fuel itself, or as an additive used therein.

Preferably, the marker compounds have a log P value of at least 3, where P is the 1-octanol/water partition coefficient. Preferably, the marker compounds have a log P of at least 4, preferably at least 5. Log P values which have not been experimentally determined and reported in the literature can be estimated using the method disclosed in Meylan, W. M & Howard, P. H., *J. Pharm. Sci.*, vol. 84, pp. 83-92 (1995).

Preferably the petroleum hydrocarbon or liquid biologically derived fuel is a petroleum hydrocarbon, biodiesel fuel or ethanol fuel; preferably a petroleum hydrocarbon or biodiesel fuel; preferably a petroleum hydrocarbon; preferably crude oil, gasoline, diesel fuel, kerosene, jet fuel or heating oil; preferably gasoline.

Preferably, the marker compounds are detected by at least partially separating them from constituents of the petroleum hydrocarbon or liquid biologically derived fuel using a chromatographic technique, e.g., gas chromatography, liquid chromatography, thin-layer chromatography, paper chromatography, adsorption chromatography, affinity chromatography, capillary electrophoresis, ion exchange and molecular exclusion chromatography. Chromatography is followed by at least one of: (i) mass spectral analysis, and (ii) FTIR. Identities of the marker compounds preferably are determined by mass spectral analysis. Preferably, mass spectral analysis is used to detect the marker compounds in the petroleum hydrocarbon or liquid biologically derived fuel without performing any separation. Alternatively, marker compounds may be concentrated prior to analysis, e.g., by distilling some of the more volatile components of a petroleum hydrocarbon or liquid biologically derived fuel.

Preferably, more than one marker compound is present. Use of multiple marker compounds facilitates incorporation into the petroleum hydrocarbon or liquid biologically derived fuel of coded information that may be used to identify the origin and other characteristics of the petroleum hydrocarbon or liquid biologically derived fuel. The code comprises the identities and relative amounts, e.g., fixed integer ratios, of the marker compounds. One, two, three or more marker compounds may be used to form the code. Marker compounds according to this invention may be combined with markers of other types, e.g., markers detected by absorption spectrometry, including those disclosed in U.S. Pat. No. 6,811,575; U.S. Pat. App. Pub. No. 2004/0250469 and EP App. Pub. No. 1,479,749. Marker compounds are placed in the petroleum hydrocarbon or liquid biologically derived fuel directly, or alternatively, placed in an additives package containing other compounds, e.g., antiwear additives for lubricants, detergents for gasoline, etc., and the additives package is added to the petroleum hydrocarbon or liquid biologically derived fuel.

The compounds of this invention may be prepared by methods known in the art, e.g., alkylation of phenols or polyhydroxyaromatics with trityl halide or alcohol, followed by alkylation with organic halides in the presence of base. For example, tritylated phenolic ethers may be prepared according to the following reaction scheme,

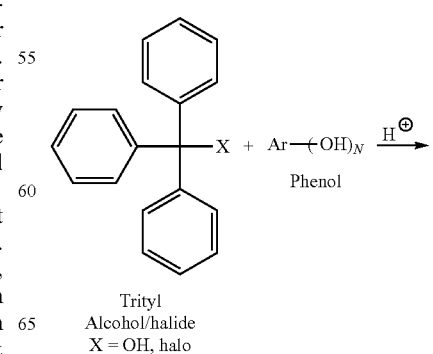

Trityl
Alcohol/halide
X = OH, halo

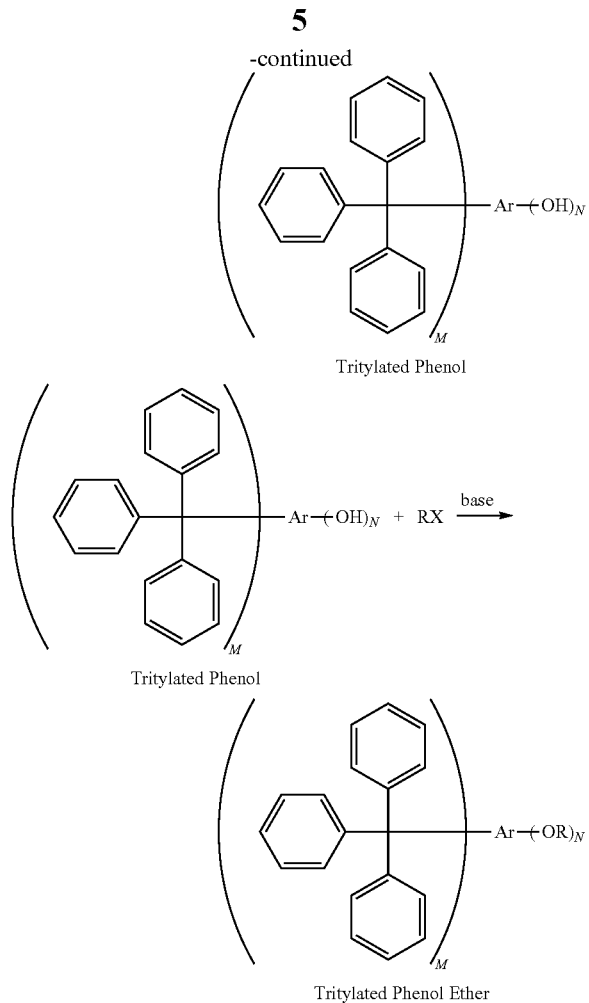

Tritylated Phenol

Tritylated Phenol

Tritylated Phenol Ether wherein M is one or two and N is 1 to 4. Corresponding compounds in which G is S may be prepared from the corresponding thiophenolic starting materials. Compounds in which G is SO or $SO_2$ may be made from the G=S compounds by oxidation.

EXAMPLES

Typical mono-tritylated phenol synthesis procedure is illustrated by the following example: 4-Tritylbenzene-1,2-diol: A 1 L 3-neck flask was equipped with a mechanical stirrer, a reflux condenser with nitrogen blanket, and a heating mantle with a temperature controller and a thermocouple. The flask was charged with 78.20 grams (0.30 moles) of trityl alcohol, 39.39 grams (0.36 moles) of catechol, and 250 mL of glacial acetic acid. The mixture was stirred under nitrogen while heating to about 80° C. A clear amber solution was obtained. To this solution were added 16.73 grams (0.06 moles) of trityl chloride in one portion. The chloride dissolved quickly. The mixture was brought to reflux. After about 30 minutes at reflux, solids began to separate out. Reflux was continued for another 5 hours before cooling to room temperature. The reaction mixture was filtered, and the grey solids were washed on the filter with several portions of acetic acid. The product was dried—first in air and finally in a vacuum oven at 60° C. for 2 hours. The yield of product was 92.0 grams (72.5%), having a melting point of 245-248° C. The structure was confirmed by IR, $^1$H- and $^{13}$C-NMR, and GC/MS analyses.

Typical bis-tritylated phenol synthesis procedure is illustrated by the following example: 4,6-Ditritylbenzene-1,3-diol: A 1 L 3-neck flask was equipped with a mechanical stirrer, a reflux condenser with nitrogen blanket, and a heating mantle with a temperature controller and a thermocouple. The flask was charged with 12.39 grams (0.0475 moles) of trityl alcohol, 15.03 grams (0.054 moles) of trityl chloride, 5.53 grams (0.05 moles) of resorcinol, and with 50 mL of glacial acetic acid. The mixture was stirred under nitrogen while heating to reflux. At about 80° C., a clear amber solution was obtained. Solids began to separate out after about 30 minutes. Reflux was continued for a total of about 34 hours. The reaction mixture was cooled to room temperature, then it was filtered. The white solids were washed on the filter with several portions of acetic acid. The product was dried—first in air for about 2 hours, and then in a vacuum oven at 50° C. for 3 hours. The yield of product was 15.27 grams (95%), having a melting point of 272-274° C. The structure was confirmed by IR, $^1$H- and $^{13}$C-NMR, and GC/MS analyses.

Scheme for the Synthesis of Functionalized Tritylated Phenol Ethers

Typical functionalized mono-tritylated phenol mono-ether synthesis procedure is illustrated by the following example:

6-(4-Tritylphenoxy)hexan-1-ol

A 25 mL 3-neck flask was equipped with a magnetic stirrer, a reflux condenser with nitrogen blanket, and a heating mantle with a temperature controller and a thermocouple. The flask was charged with 1.12 grams (0.0033 moles) of 4-tritylphenol, 0.22 grams (0.0033 moles, 85 wt. %) of potassium hydroxide pellets, and with 5 mL of dimethylsulfoxide. The mixture was stirred under nitrogen while heating to 100° C. After about 2 hours, all of the potassium hydroxide had dissolved, and the mixture was cooled to 70° C. 6-Chlorohexanol (0.45 grams, 0.0033 moles) was then added in one portion. The reaction mixture was maintained at 100° C. for about 0.5 hours, then it was stirred at room temperature overnight. A sample withdrawn for GC analysis at this point showed no remaining starting materials, indicating that the reaction was completed. The reaction mixture was poured into 100 mL of water. Solids precipitated. The mixture was filtered. The beige solids were washed on the filter with several portions of water, then they were air-dried. The yield of product was 1.2 grams (83%). The structure was confirmed by IR, $^1$H- and $^{13}$C-NMR, and GC/MS analyses.

Typical functionalized mono-tritylated phenol bis-ether synthesis procedure is illustrated by the following example:

6,6'-((4-trityl-1,2-phenylene)bis(oxy))bis(hexan-1-ol)

A 100 mL 3-neck flask was equipped with a magnetic stirrer, a reflux condenser with nitrogen blanket, and a heating mantle with a temperature controller and a thermocouple. The flask was charged with 3.52 grams (0.01 moles) of 4-tritylbenzene-1,2-diol, 1.32 grams (0.02 moles, 85 wt. %) of potassium hydroxide pellets, and with 25 mL of dimethylsulfoxide. The mixture was stirred under nitrogen while heating to 105° C. until the potassium hydroxide pellets had dissolved. The mixture was cooled to 55° C., then 6-chlorohexanol (2.73 grams, 0.02 moles) was added in one portion. An exotherm to about 58° C. was observed. After the exotherm subsided, the reaction mixture was maintained at 65° C. for about 2 hours. A sample withdrawn for GPC analysis at this point showed about 83% conversion to the bis-ether. The presence of unreacted 4-tritylbenzene-1,2-diol suggested that some of the chlorohexanol had cyclized to oxepane; an additional 0.5 grams (0.0037 moles) of chlorohexanol was added to the reaction mixture, and heating at 60° C. was continued. After 5.5 hours, the reaction mixture was poured into 400 mL of water. The product separated as an oil. The mixture was extracted with about 2×75 mL of toluene. The toluene layers were combined, and were then washed with 1×50 mL of saturated aqueous sodium chloride solution. After drying over anhydrous magnesium sulfate, the toluene was removed by rotary evaporation to give 1.97 grams of beige solid product (36% yield). MP=81-84° C. The structure was confirmed by IR, $^1$H- and $^{13}$C-NMR, and GC/MS analyses.

Using the above procedure, the following functionalized tritylated phenol ethers were prepared:

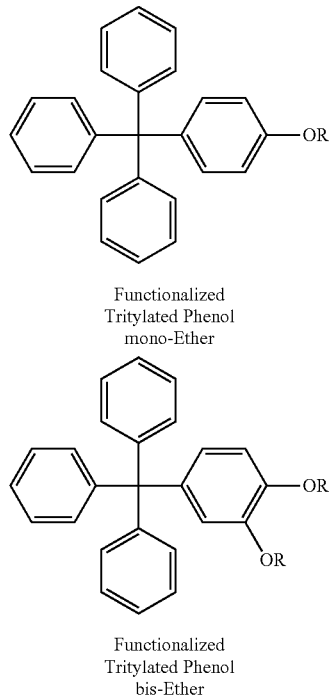

Functionalized Tritylated Phenol mono-Ether

Functionalized Tritylated Phenol bis-Ether

TABLE 1

Synthesis Data for Functionalized Tritylated Phenol Ethers

| Ex. No. | | % Yield | MP, ° C. |
|---|---|---|---|
| | Functionalized Tritylated Phenol mono-Ethers: R | | |
| 1 | (CH$_2$)$_6$OH | 83 | 158-161 |
| 2 | (CH$_2$)$_2$O(CH$_2$)$_2$OH | 93 | 144-146 |
| | Functionalized Tritylated Phenol bis-Ethers: R | | |
| 3 | (CH$_2$)$_4$OH | <10 | oil |
| 4 | (CH$_2$)$_6$OH | 36 | 81-84 |
| 5 | (CH$_2$)$_2$O(CH$_2$)$_2$OH | 89 | oil |

GC/MS Studies:

Stock solutions of functionalized tritylated phenol ethers were prepared in dichloromethane (DCM). These solutions were used to establish GC retention times and MS fragmentation patterns. The results are shown in Table 2.

GC/MS Parameters:
Column: Agilent DB 35 m, 15.0 m×0.25 mm×0.25μ
Flow Rate: 1.5 mL/min. He carrier gas
Oven: initial: 100° C.
Ramp 1: 20° C./min to 280° C.; Hold: 10 min
Ramp 2: 20° C./min to 340° C.; Hold: 6 min.
Inlet Temp.: 280° C.
Insert: Splitless; Vent: 15 min., Single taper, glass wool, deactivated, 5062-3587
Injection Volume: 3 μL; Viscosity: 5 sec., Plunger: fast
Mass Transfer Line Temp.: 280° C.
MS Quad: 200° C.; MS Source: 250° C.
Solvent Delay: 18.5 min

TABLE 2

GC/MS Data for Functionalized Tritylated Phenol Ethers

| Ex. No. | | GC Retention Time, min. | Major Mass, m/e |
|---|---|---|---|
| | Functionalized Tritylated Phenol mono-Ethers: R | | |
| 1 | (CH$_2$)$_6$OH | 21.72 | 436, 359, 259 |
| 2 | (CH$_2$)$_2$O(CH$_2$)$_2$OH | 20.42 | 424, 347, 259 |
| | Functionalized Tritylated Phenol bis-Ethers: R | | |
| 4 | (CH$_2$)$_6$OH | 28.29 | 552, 375, 275 |
| 5 | (CH$_2$)$_2$O(CH$_2$)$_2$OH | 25.16 | 528, 451, 363 |

Solubility Studies:

The solubility properties of functionalized tritylated phenol ethers were determined by mixing 0.1 gram samples of sample in 0.9 grams of solvent. The mixtures were warmed at 60° C. for a few minutes to make homogeneous solutions. The solutions were cooled back to room temperature, and then they were placed into a freezer at −10° C. The solutions were checked daily to see if crystallization had occurred.

| Compound | Solvent | wt % | 60 C. | RT | −10 C. |
|---|---|---|---|---|---|
| Ex. 4 | AROMATIC 200 | 10 | insoluble | insoluble | |
| | Tetralin | 10 | soluble | insoluble | |
| | DPGME | 10 | soluble | soluble | crystals after 6 days |
| | NMP | 10 | soluble | soluble | soluble after 7 days |
| | DMAc | 10 | soluble | soluble | soluble after 7 days |
| | 1-Octanol | 10 | soluble | soluble | crystals after 1 day |
| Ex. 5 | AROMATIC 200 | 10 | soluble | soluble | soluble after 7 days |
| | Tetralin | 10 | soluble | soluble | soluble after 7 days |
| | DPGME | 10 | soluble | soluble | soluble after 7 days |
| | NMP | 10 | soluble | soluble | soluble after 7 days |
| | DMAc | 10 | soluble | soluble | soluble after 7 days |

DPGME is dipropylene glycol mono-methyl ether and NMP is N-methylpyrrolidone; AROMATIC 200 is a mixed aromatic solvent available from Exxon Mobil Corp.

The invention claimed is:

1. A compound having formula (Ph$_3$C)$_m$Ar(GR)$_n$, wherein Ph represents a phenyl group, Ar is an aromatic ring system having from six to twenty carbon atoms; G is O, S, SO or SO$_2$;

R is: (a) $C_3$-$C_{12}$ alkyl substituted by at least one of OH, SH and $C_1$-$C_6$ alkoxy; or (b) $C_4$-$C_{12}$ heteroalkyl; m is one or two; and n is two.

2. The compound of claim 1 in which Ar is a $C_6$-$C_{12}$ hydrocarbyl aromatic ring system.

3. The compound of claim 2 in which R is $C_4$-$C_8$ heteroalkyl not containing sulfur and G is O.

4. The compound of claim 3 in which Ar is a benzene ring system.

5. A method for marking a petroleum hydrocarbon or a liquid biologically derived fuel; said method comprising adding to said petroleum hydrocarbon or liquid biologically derived fuel at least one compound having formula $(Ph_3C)_m Ar(GR)_n$, wherein Ph represents a phenyl group, Ar is an aromatic ring system having from six to twenty carbon atoms; G is O, S, SO or $SO_2$; R is: (a) $C_1$-$C_{18}$ alkyl substituted by at least one of OH, SH, $C_1$-$C_{18}$ alkoxy and cyano; or (b) $C_4$-$C_{18}$ heteroalkyl; m is one or two; and n is an integer from one to four, wherein each compound having formula $(Ph_3C)_m Ar(GR)_n$ is present at a level from 0.01 ppm to 20 ppm.

6. The method of claim 5 in which Ar is a $C_6$-$C_{12}$ hydrocarbyl aromatic ring system and R is $C_4$-$C_{18}$ heteroalkyl.

7. The method of claim 6 in which n is an integer from one to three.

8. The method of claim 7 in which R is $C_4$-$C_8$ heteroalkyl not containing sulfur and G is O.

9. The method of claim 8 in which Ar is a benzene ring system and n is two.

10. The compound of claim 2 in which G is O.

11. The compound of claim 10 in which Ar is a benzene ring system.

\* \* \* \* \*